United States Patent
Cetinkaya et al.

(10) Patent No.: US 11,996,185 B1
(45) Date of Patent: May 28, 2024

(54) CANISTER CONFIGURATION SYSTEM FOR MEDICATION DISPENSING MACHINES

(71) Applicant: Amazon Technologies, Inc., Seattle, WA (US)

(72) Inventors: Elcin Cetinkaya, Seattle, WA (US); Jianfeng Liu, Shoreline, WA (US); Richard Voskoboynikov, Pembroke Pines, FL (US)

(73) Assignee: Amazon Technologies, Inc., Seattle, WA (US)

( * ) Notice: Subject to any disclaimer, the term of this patent is extended or adjusted under 35 U.S.C. 154(b) by 308 days.

(21) Appl. No.: 17/449,415

(22) Filed: Sep. 29, 2021

(51) Int. Cl.
*G16H 40/20* (2018.01)
*A61J 7/00* (2006.01)
*G06F 17/18* (2006.01)
*G06Q 10/0631* (2023.01)
*G16H 20/13* (2018.01)
*G16H 40/40* (2018.01)
*G16H 50/70* (2018.01)

(52) U.S. Cl.
CPC ............ *G16H 40/20* (2018.01); *A61J 7/0084* (2013.01); *G06Q 10/06313* (2013.01); *G16H 20/13* (2018.01); *G16H 40/40* (2018.01); *G16H 50/70* (2018.01); *G06F 17/18* (2013.01)

(58) Field of Classification Search
CPC ........ G16H 40/20; G16H 20/13; G16H 40/40; G16H 50/70; A61J 7/0084; G06Q 10/06313; G06F 17/18
See application file for complete search history.

(56) References Cited

U.S. PATENT DOCUMENTS

| | | |
|---|---|---|
| 6,611,733 B1 * | 8/2003 | De La Huerga ............................ G06K 19/07762 700/235 |
| 9,926,131 B1 | 3/2018 | Lehmann |
| 10,593,425 B1 | 3/2020 | Truscott et al. |
| 10,807,767 B1 | 10/2020 | Kriesel et al. |
| 10,998,094 B1 | 5/2021 | Chiu et al. |

(Continued)

OTHER PUBLICATIONS

D. Craswell, Alison, et al. "The Impact of Automated Medicine Dispensing Units on Nursing Workflow: A Cross-Sectional Study." International journal of nursing studies 111 (2020): 3773 (Year: 2020).*

*Primary Examiner* — Amber A Misiaszek
(74) *Attorney, Agent, or Firm* — Knobbe, Martens, Olson & Bear, LLP (57) ABSTRACT

Systems and methods are described for providing a canister configuration system for medication dispensing machines. A medication dispensing machine has capacity to hold a fixed number of canisters and trays, each of which may contain a particular medication. If an order is received for a medication that is not in one of the currently loaded canisters, a canister of that medication may be swapped in, or the medication may be dispensed from a tray. A canister configuration system may analyze received orders, dispensed medications, and other inputs and constraints, and may determine a canister configuration for one or more dispensing machines that reduces canister swaps and tray fills. The canister configuration(s) may specify groups of medications that should be dispensed in particular ways, such as via canisters that remain in the dispensing machine at all times, via canisters that are swapped in or out as needed, or via trays.

20 Claims, 6 Drawing Sheets

(56) References Cited

U.S. PATENT DOCUMENTS

| | | | |
|---|---|---|---|
| 2003/0050731 A1* | 3/2003 | Rosenblum | G07F 17/0092 700/232 |
| 2005/0049746 A1* | 3/2005 | Rosenblum | G16H 20/13 700/232 |
| 2007/0135965 A1* | 6/2007 | Nguyen | A61G 12/001 700/231 |
| 2008/0086235 A1* | 4/2008 | Frankel | G07F 17/12 700/244 |
| 2012/0239824 A1* | 9/2012 | Nguyen | H04L 51/56 709/246 |
| 2016/0026917 A1 | 1/2016 | Weisberg et al. | |
| 2017/0199983 A1 | 7/2017 | Cano et al. | |
| 2017/0275035 A1 | 9/2017 | Luciano, Jr. | |
| 2018/0261312 A1 | 9/2018 | Dake et al. | |
| 2020/0098457 A1 | 3/2020 | Naygauz | |
| 2021/0086947 A1 | 3/2021 | Kriesel et al. | |
| 2021/0098104 A1 | 4/2021 | Truscott et al. | |

\* cited by examiner

CANISTER CONFIGURATION SYSTEM FOR MEDICATION DISPENSING MACHINES

BACKGROUND

Generally described, medication dispensing machines may be used to fulfill orders for medications. A medication dispensing machine may have capacity to hold a number of canisters, from which individual medications can be dispensed. A medication dispensing machine may also have a tray or trays from which medication can be dispensed on an as-needed basis (e.g., to fulfill a particular order). The capacity of the medication dispensing machine to hold canisters is generally lower than the number of medications that can be ordered.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION

Generally described, aspects of the present disclosure relate to improving the performance of medication dispensing machines. More specifically, aspects of the present disclosure are directed to systems, methods, and computer-readable media related to a canister configuration system, which configures medication dispensing machines to reduce operations that impact the performance of the machines. In a common embodiment, a medication dispensing machine has a fixed number of slots N into which canisters of medications can be loaded. Each canister may contain a particular medication, and the dispensing machine may thus be configured to dispense up to N different medications from canisters at any given time. However, the number of medications that can be ordered is generally significantly higher than the capacity N of an individual dispensing machine. Fulfillment of individual orders may also require that multiple medications be dispensed, and it is generally not practical to move a partially filled order from one dispensing machine to another given the number of possible variations that may occur and/or when the medication is to be dispensed into certain types of packaging. For example, some fulfillment processes are preformed using strips of connected, perforated daily dose packets that cannot easily be removed from a dispensing machine and remounted to another dispensing machine during a filling procedure.

Orders for medications are thus typically filled by swapping canisters on the dispensing machine, or, for some medications, by filling the order from a tray. However, canister swaps and tray fills generally require that the dispensing machine pause until an operator has loaded the relevant canister(s) into the machine or placed the relevant medication(s) into a tray or trays. Canister swaps and tray fills thus represent inefficiencies in the operation of a medication dispensing machine, and it is desirable to minimize these inefficiencies in order to improve the performance of the machine.

An operator of medication dispensing machines may therefore implement a container configuration system as described herein, and thereby improve the performance of a medication dispensing machine by reducing canister swaps and tray fills. As described in more detail below, the canister configuration system may analyze past medication orders (or, in some embodiments, may obtain predictions or predict future orders) to implement a canister configuration that minimizes canister swaps, tray fills, and otherwise reduces operations that negatively impact the performance of a medication dispensing machine.

While the present disclosure includes examples in which machines dispense medications from canisters, it will be understood that the present disclosure is not limited to a particular type of medication dispensing machine or a particular type of container from which medications are dispensed. Embodiments of the present disclosure include, for example, machines that dispense medications from canisters, cells, trays, hoppers, and other such containers.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
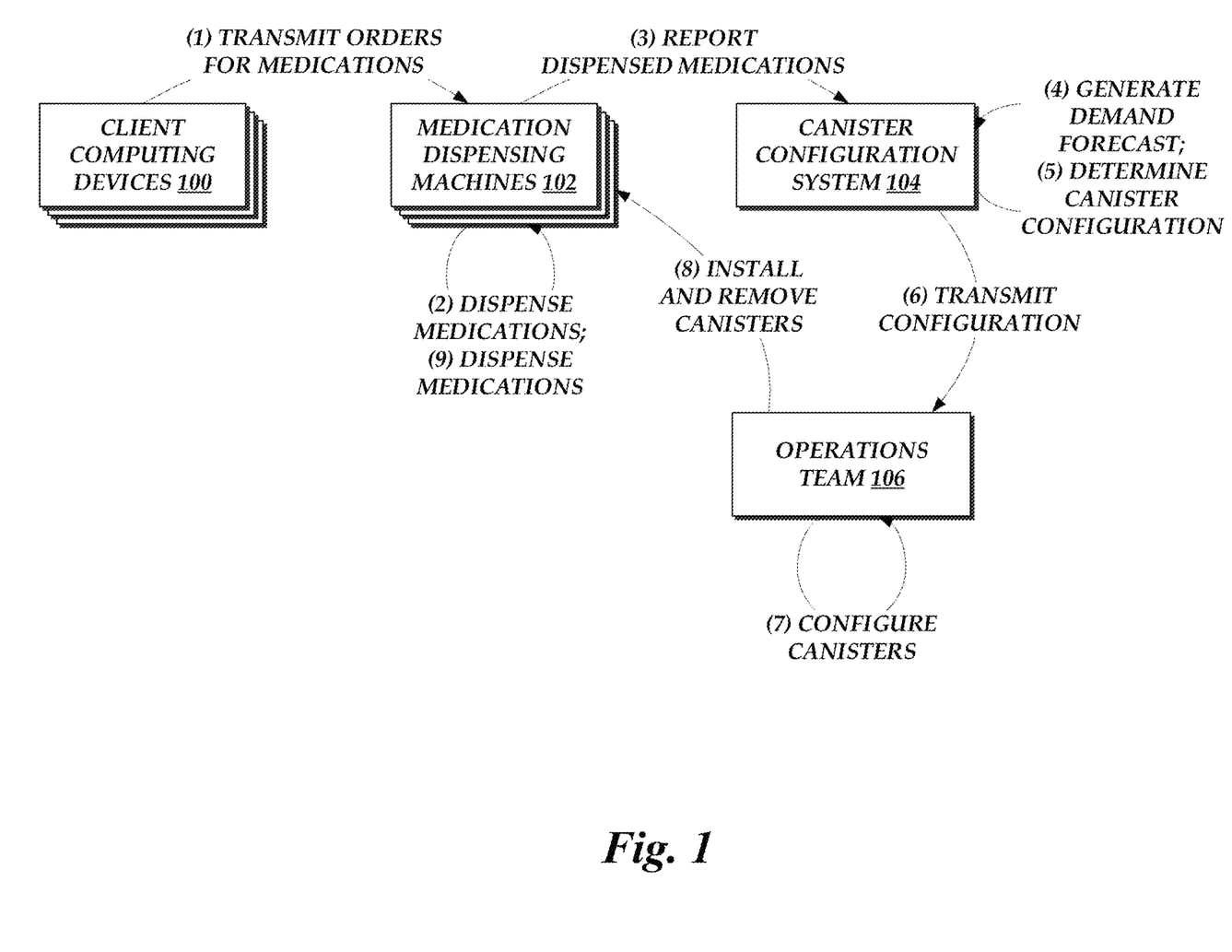
FIG. 1 is a flow diagram depicting example interactions for configuring a medication dispensing machine in accordance with aspects of the present disclosure.

FIG. 1 depicts example interactions for configuring a medication dispensing machine in accordance with aspects of the present disclosure. As discussed, above, the example interactions may improve the performance of a medication dispensing machine by reducing the number of canister swaps or tray fills that must be performed during operation of the machine, thereby allowing the machine to dispense medications more efficiently. The example interactions begin at (1), where client computing devices 100 may transmit orders for medications that are received by medication dispensing machines 102. In some embodiments, orders from client computing devices 100 may be transmitted to medication dispensing machines 102 via intermediary devices, such as a computing device that receives and processes orders, a load balancer, or other such devices. In further embodiments, orders may be transmitted via a network, such as the network 510 depicted in FIG. 5.

At (2), the medication dispensing machines 102 may dispense medications in accordance with the orders that were received at (1). Illustratively, an order for a medication or medications may be received by a particular medication dispensing machine 102, which may dispense medications from canisters that are already slotted into the machine 102. In some embodiments, the machine 102 may prompt a technician to swap canisters or load a needed medication via a tray fill so that all of the medications needed to fulfill an order may be dispensed.

At (3), the medication dispensing machines 102 (or, in some embodiments, a logging device or other intermediary device) may report which medications have been dispensed by each machine 102 to a canister configuration system 104. Illustratively, the report may indicate the quantities of each medication (e.g., the number of pills) that were dispensed, and in some embodiments may indicate quantities of medication dispensed on a per-order basis. For example, the report may indicate that a first order included 20 pills of medication X, 40 pills of medication Y, and 10 pills of medication Z; that a second order included 30 pills of medication X; and that a third order included 15 pills of medication Y and 24 pills of medication A. In some embodiments, the report may indicate the canister or slot from which a medication was dispensed in addition to or instead of indicating the medication, or the report may indicate that a particular medication was dispensed from a tray fill. Additionally, in some embodiments, the report may indicate on a per-order basis whether a canister was "swapped in" to fulfill the order. In some embodiments, canister configuration system 104 may obtain the report from the medication dispensing machines 102 (or from a logging device or other intermediary device) rather than the medication dispensing machines 102 transmitting the report. In further embodiments, the report may be obtained or transmitted periodically (e.g., weekly or monthly), after a threshold quantity of medications have been dispensed, or according to another schedule.

At (4), the canister configuration system 104 may generate (or, in some embodiments, obtain) a demand forecast of future orders that will be received and fulfilled by the medication dispensing machines 102. In some embodiments, the demand forecast corresponds to the report received at (3). For example, the orders forecasted for the next 30 days may correspond to the orders received in the past 30 days. In other embodiments, the demand forecast may be generated based in part on factors such as the time of year (e.g., that allergy medications are likely to be ordered at certain times), trends in the data (e.g., that orders for a particular medication are increasing or decreasing), external data such as price changes or approved uses, or other factors.

At (5), the canister configuration system 104 may determine a canister configuration for the medication dispensing machine 102. In some embodiments, the canister configuration system 104 may determine a canister configuration by determining a solution to a mixed-integer linear programming problem that seeks to minimize an objective function that is based on a set of weighting factors. For example, the canister configuration system 104 may seek to minimize the objective function $\Sigma_m \Sigma_g (c_{m,g}^{flex} + c_{m,g}^{tray}) + W_{recon} \cdot \Sigma_m \Sigma_t n_{m,t}^{recon}$, where m indexes a set of medications, g indexes a set of medication dispensing machine groups, $c_{m,g}^{flex}$ is a weighting factor representing a cost, in terms of fill procedure efficiency, associated with swapping in a canister of medication m on a dispensing machine from group g, $c_{m,g}^{tray}$ is a weighting factor/cost associated with a tray fill of medication m on a dispensing machine from group g, $W_{recon}$ is a weighting factor/cost associated with reconfiguring a canister (which in various embodiments may include removing an existing medication from the canister, cleaning the canister, loading a new medication into the canister, physically or virtually (re)labeling the canister, and the like), t indexes a set of canister types (e.g., canisters for dispensing small pills, canisters for dispensing large pills, high capacity canisters, low capacity canisters, canisters that fit into a particular medication dispensing machine, and combinations thereof), and $n_{m,t}^{recon}$ is a weighting factor representing a number of reconfigurations of a canister of type t to dispense medication m. It will be understood by one skilled in the art that the aforementioned mixed-integer linear programming problem and set of weighting factors are provided for purposes of example, and that other weighting factors and minimization techniques are within the scope of the present disclosure. For example, a machine learning model or a Monte Carlo simulation may be used to determine a canister configuration that minimizes a set of weighting factors. As a further example, the canister configuration system 104 may determine a solution to a mixed-integer linear programming problem that seeks to maximize an objective function that represents fill procedure efficiency rather than seeking to minimize an objective function that represents inefficiencies.

At (6), the canister configuration system 104 may transmit the determined canister configuration to an operations team 106 responsible for implementing canister configurations. At (7), the operations team 106 may configure the canisters in accordance with the canister configuration received at (6), and at (8) the operations team 106 may configure the medication dispensing machines 102 by loading or removing canisters as needed to conform with the updated canister configuration. At (9), the reconfigured medication dispensing machines 102 may dispense medications in accordance with the new and more efficient configuration.

It will be understood that FIG. 1 is provided for purposes of example, and that many variations on the depicted interactions are within the scope of the present disclosure. For example, the canister configuration system 104 may obtain a report of dispensed medications indirectly rather than the report being transmitted by the medication dispensing machines 102. As a further example, the interaction at (4) may be omitted and the canister configuration system 104 may determine an optimal canister configuration based on recently fulfilled orders rather than attempting to predict future orders. As a further example, the interactions of configuring canisters at (7) and installing/removing canisters at (8) may be automated (e.g., using robotic devices) rather than performed manually. FIG. 1 is thus understood to be illustrative and not limiting.

Figure 2:
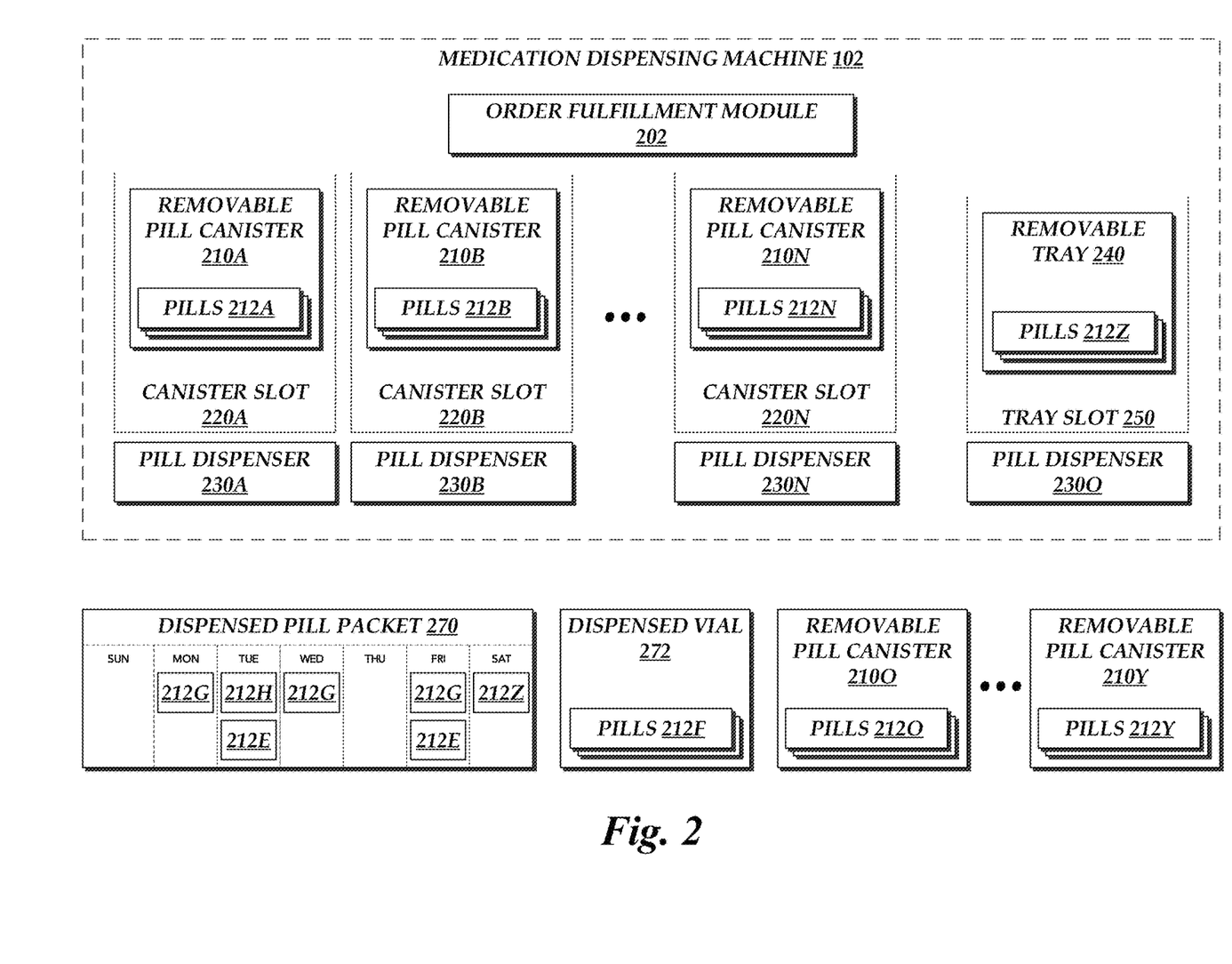
FIG. 2 is a block diagram depicting a general architecture of a medication dispensing machine that may be configured in accordance with aspects of the present disclosure.

FIG. 2 is a block diagram depicting an environment including an example medication dispensing machine 102 and dispensed medications 270 and 272. In the depicted embodiment, the medication dispensing machine 102 includes an order fulfillment module 202, which may receive and fulfill orders for particular medications. The medication dispensing machine 102 further includes a number of canister slots 220A-N, each of which may contain a removable pill canister 210A-N. Each of the removable pill canisters 210A-N may in turn contain a number of pills 212A-N, which may be dispensed by the pill dispensers 230A-N. The quantity of canister slots 220A-220N and corresponding pill dispensers 230A-230N of a particular medication dispensing machine 102 may be predefined and substantially static, thereby imposing an upper limit on the quantity of removable pill canisters 210A-210N that may be installed in the medication dispensing machine 102 at any given time. It will be understood that the range A-N has been chosen for purposes of example and that the present disclosure is not limited to a particular quantity of these components.

The environment depicted in FIG. 2 further includes a number of removable pill canisters 210O-Y, which contain quantities of pills 212O-Y. The removable pill canisters 210O-Y may be identical in function to the canisters 210A-N that are currently loaded into canister slots 220A-N, and at various times during the operation of the medication dispensing machine 102 one of the canisters 210O-Y may be swapped with one of the canisters 210A-N so that the machine 102 may fulfill a particular order that includes one of the medications 212O-Y. Swapping the canisters requires time and effort, and in some embodiments may cause the medication dispensing machine 102 to stop fulfilling orders until a needed canister 210O-Y has been loaded. It is therefore desirable to minimize the number of canister swaps that must be performed.

The medication dispensing machine 102 may further include a number of tray slots 250 holding removable trays 240, each of which may hold a number of pills 212Z that may be dispensed by a dispenser 230O. Illustratively, the trays 240 may be used to dispense small amounts of medication to fulfill a particular order when one (or more) of the medications needed to fulfill the order is not available to be dispensed from a canister 210A-Y. In some embodiments, trays are filled (e.g., with pills 212Z) manually and on an as-needed basis when an order is received for a medication that is not available from one of the canisters 210A-Y. However, the manual tray-filling process may be slower and subject to higher error rates than canister-based order fulfillment, making it desirable to minimize the number of tray fills that must be performed.

Each of the removable pill canisters 210A-Y may be configured to store a particular pill 212A-Y. For example, in some embodiments, a particular pill 212J may be physically larger or smaller than average, or may have a shape that requires a particular configuration of the canister 210J to ensure that the correct quantity of the pill 212J is dispensed. In some embodiments, as discussed above, the canisters 210A-Y may be of different types. For example, the canisters 210A-G may be of a type that fits into the slots of a particular medication dispensing machine 102, and the canisters 210R-Y may be of a different type that does not fit. As a further example, the canisters 210H-K may be of a type that dispenses pills 212H-K that are physically larger or smaller. In some embodiments, particular canister types may be associated with particular medication dispensing machines 102.

The environment depicted in FIG. 2 also includes a dispensed pill packet 270 and a dispensed vial 272, which are examples of dispensed medications that may fulfill a particular order. The dispensed pill packet 270 may illustratively contain a number of different medications, such as pills 212E, 212G, 212H, and 212Z, and in some embodiments may be compartmentalized or otherwise partitioned into particular dosages. In the depicted embodiment, the dispensed pill packet 270 contains a medication (pill 212Z) that was not loaded into one of the canisters 210A-Y and was instead dispensed from a removable tray 240. The dispensed vial 272, by contrast, contains a single medication (pills 212F). In various embodiments, a particular medication dispensing machine 120 may dispense pill packets 270, vials 272, or both, and may fulfill orders using any combination thereof.

It will be understood that FIG. 2 highlights a number of features of a medication dispensing machine 102 that are relevant to the present disclosure, and that a medication dispensing machine 102 may include significantly more components than those depicted in FIG. 2 without departing from the present disclosure.

Figure 3:
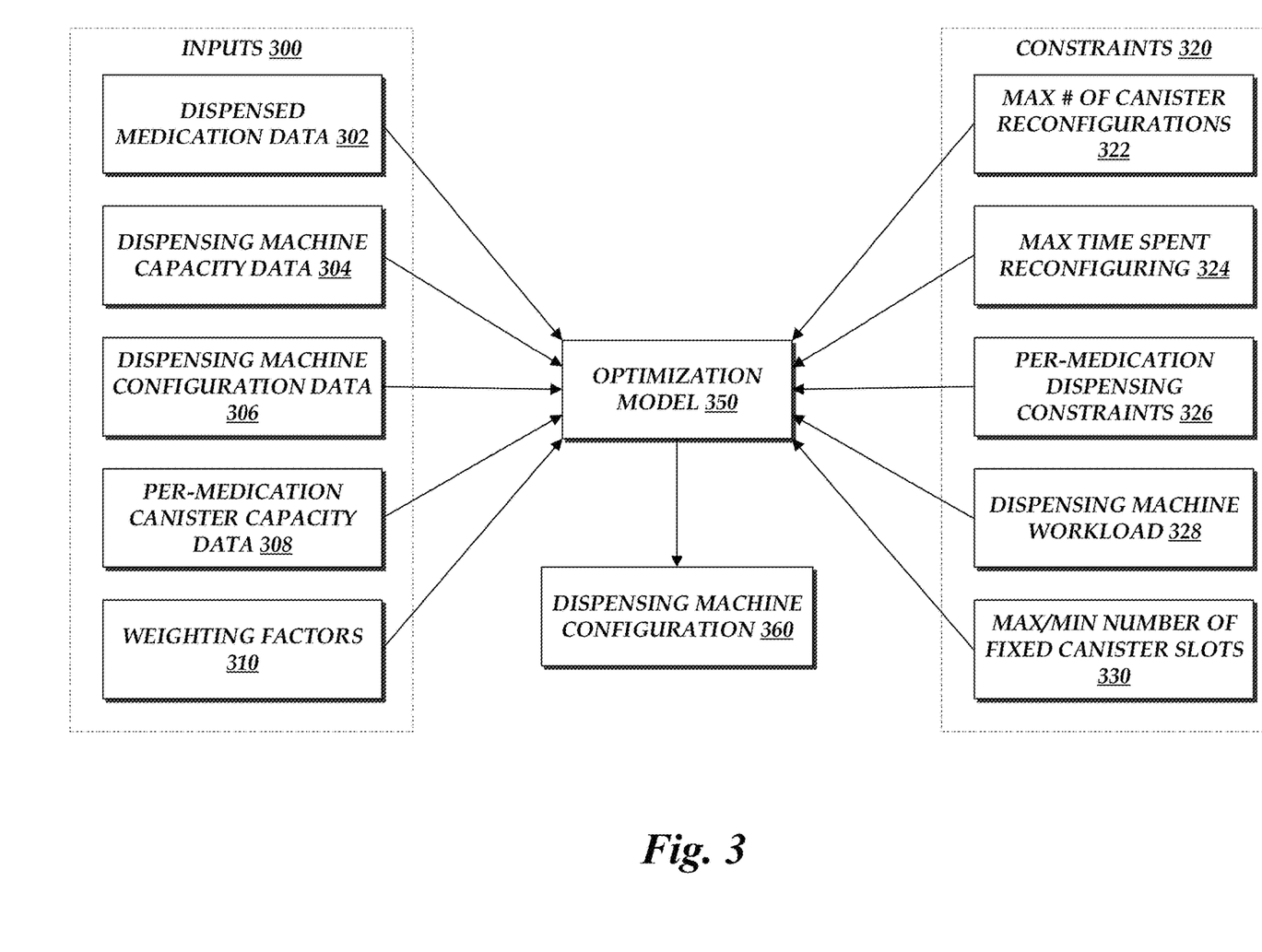
FIG. 3 is a block diagram depicting an example model for determining a medication dispensing machine configuration in accordance with aspects of the present disclosure.

FIG. 3 is a block diagram depicting an example model for configuring a medication dispensing machine in accordance with aspects of the present disclosure. As depicted, the optimization model 350 receives a number of inputs 300 and constraints 320 that it processes to determine a dispensing machine configuration 360. The inputs 300 may include, for example, dispensed medication data 302 representing medications dispensed by one or more dispensing machines 102. In some embodiments, medication dispensing machines 102 may be organized into groups or categories, and the dispensed medication data 302 may be broken out by group or category. For example, the dispensed medication data 302 may include data for a first group of machines 102 that dispense vials of individual medications and for a second group of machines 102 that dispense packets containing multiple medications. As a further example, the medication dispensing machines 102 may be categorized according to the types of canisters they can accept, and the dispensed medication data 302 may be broken out accordingly. In some embodiments, a demand forecast may be received rather than or in addition to the dispensed medication data 302.

In some embodiments, the dispensed medication data 302 and/or the demand forecast may be broken out into individual orders for medications, with each order containing quantities of one or more medications. For example, the dispensed medication data 302 may indicate that a first order was received and fulfilled for 10 pills 212A, 20 pills 212B, and 30 pills 212C. Such data may be used by the optimization model 350 to ensure that at least one dispensing machine 102 is configured with canisters containing pills 212A, 212B, and 212C, so that a single dispensing machine 102 is configured to fulfill orders for these three pills. In some embodiments, the dispensed medication data 302 may indicate whether individual medications were dispensed from a canister 210A-Y or a tray 240, or may indicate whether (or how many times) a canister 210A-Y was swapped into a machine 102 to fulfill individual orders as they came in.

The inputs 300 to the optimization model 350 may, in some embodiments, include dispensing machine capacity data 304. The dispensing machine capacity data 304 may illustratively include quantities and types of canisters 210A-Y that a particular machine 102 can accept. For example, the capacity data 304 may indicate that a particular dispensing machine 102 has 20 slots that can accept canisters of type X or Y. In some embodiments, the capacity data 304 may indicate that a particular dispensing machine 102 (or group or type of dispensing machines 102) cannot dispense a particular medication from canisters or cannot dispense a particular medication at all. For example, a particular pill 212D may be relatively fragile, or may have a shape or size that is incompatible with dispensing machines 102 from a particular manufacturer. The capacity data 304 may further include numbers of tray slots 240, estimated throughputs of individual dispensing machines 102, or other information relating to capacity Additionally, in some embodiments, the dispensing machine capacity data 304 may be determined or inferred. For example, the optimization model 350 may receive configuration data 306 identifying the canisters that are currently loaded on the machine 102, and may determine or infer that the machine 102 is loaded to capacity. As a further example, the optimization model 350 may determine the throughput of a dispensing machine 102 based on the quantities of medications dispensed within a specified time period.

The inputs 300 to the optimization model 350 may further include dispensing machine configuration data 306, which may include the numbers and types of canisters 210A-Y that are currently loaded into individual medication dispensing machines 102. The configuration data 306 may include, in some embodiments, indications of which canisters 210A-Y have been designated as "fixed" canisters and are typically only removed to refill the canister, and which have been designated as "swappable" and are currently loaded in response to recent orders.

The inputs 300 may further include per-medication canister capacity data 308, which in some embodiments may be used by the optimization model 350 to determine whether a dispensing machine 102 should be loaded with two or more canisters containing the same medication. Illustratively, a machine 102 may be loaded with multiple canisters of a pill 212F that is frequently dispensed, so that an empty or almost-empty canister 210F can be refilled while another canister 210F of the same pill 212F remains available for dispensing. In some embodiments, the canister capacity data 308 may be used by the optimization model 350 to determine whether a particular pill 212D should be loaded into a higher-capacity canister or a lower-capacity canister.

The inputs 300 may further include weighting factors 310, which may be used to quantify the performance impact (e.g., "cost") of canister swaps, tray fills, canister refills, manually dispensing medications (e.g., without the use of a dispensing machine 102), converting medications from tray fill to canister fill, or vice versa. In some embodiments, the optimization model 350 may determine or infer the weighting factors 310 based on the dispensed medication data 302, which may be used as performance metrics for a particular dispensing machine 102. As described in more detail below, the optimization model 350 may generate the dispensing machine configuration 360 in part by seeking to minimize the weighting factors 310.

The optimization model 350 is also subject to a number of constraints 320 on the dispensing machine configuration(s) 360. It will be understood that the constraints 320 may also be considered "inputs" to the model 350, and are characterized as "constraints" in that they constrain the output of the model 350 rather than because they are received in a different form or format. The constraints 320 may include, for example, a maximum number of canister reconfigurations 322, which may represent a maximum number of canisters to be swapped during implementation of the update dispensing machine configuration 360. The updated dispensing machine configuration 360 may thus be constrained in how much it can differ from the existing dispensing machine configuration 306. In some embodiments, the constraints 320 may include that a particular canister cannot be omitted from the configuration 360 until X days after it was originally loaded onto the dispensing machine 102, which may prevent a canister "on the margin" from being repeatedly added to and removed from the configuration.

The constraints 320 may also include a maximum time spent reconfiguring canisters 324, which may represent a limit on the amount of time or other resources (e.g., personnel) that can be dedicated to reconfiguration for a given time interval. For example, the operations team may have a limited window during which reconfigurations can be performed, and the maximum time 324 may correspond to the length of the window. In some embodiments, the optimization model 350 may obtain or determine time intervals for reconfiguring canisters on a per-medication basis. Certain medications may take more or less time to be loaded into a canister depending on factors such as pill size and shape, the time required to configure the canister to dispense pills one at a time, and so forth.

The constraints 320 may also include per-medication dispensing constraints 326. Illustratively, some medications may have attributes that limit the manner in which they can be dispensed. For example, a dispensing constraint 326 may specify that a particular medication is a controlled substance. A canister containing the medication must therefore be loaded onto the dispensing machine 102 only when fulfilling an order for that medication, and then removed and securely stored thereafter. As further examples, a dispensing constraint 326 may specify that a particular medication can be dispensed from trays only, or that orders for it can only be fulfilled manually. In some embodiments, a dispensing constraint 326 may specify that a first medication must be dispensed in the same manner as a second medication, such that medications that are commonly prescribed together must be dispensed in the same manner. Such constraints may recognize, for example, that putting only one of the two medications into a fixed canister does not significantly improve the efficiency of the dispensing machine 102, since the other medication must be swapped in when fulfilling orders for the medications.

In some embodiments, the constraints 320 may include dispensing machine workload constraints 328. In various embodiments, the dispensing machine configuration 360 may be constrained such that each dispensing machine 102 has a minimum workload, a maximum workload, that the workloads of each dispensing machine 102 are within a specified range or percentage of each other, or other constraints to balance the workloads of the dispensing machines 102.

The constraints 320 may also include constraints on the number of fixed canister slots 330, which may include a minimum number, maximum number, allowable range, or in some embodiments a minimum, maximum, or allowable range of "flex" canister slots that are set aside for medications that are swapped in on an as-needed basis. Various combinations on the aforementioned constraints (e.g., a maximum number of fixed canister slots and a minimum number of flex canister slots) are within the scope of the present disclosure.

It will be understood that FIG. 3 is provided for purposes of example, and that other inputs and constraints beyond those depicted are within the scope of the present disclosure. For example, the inputs 300 may include expiration dates for particular stocks of medications, and the optimization model 350 may determine that the existing stock of a particular medication should or should not be loaded into a canister based on its expiration date. As a further example, the constraints 320 may include a limit on the number of different configurations to be output (e.g., that all dispensing machines 102 in a particular group have the same configuration, that they have no more than N different configurations, etc.). FIG. 3 is thus understood to be illustrative and not limiting.

Figure 4:
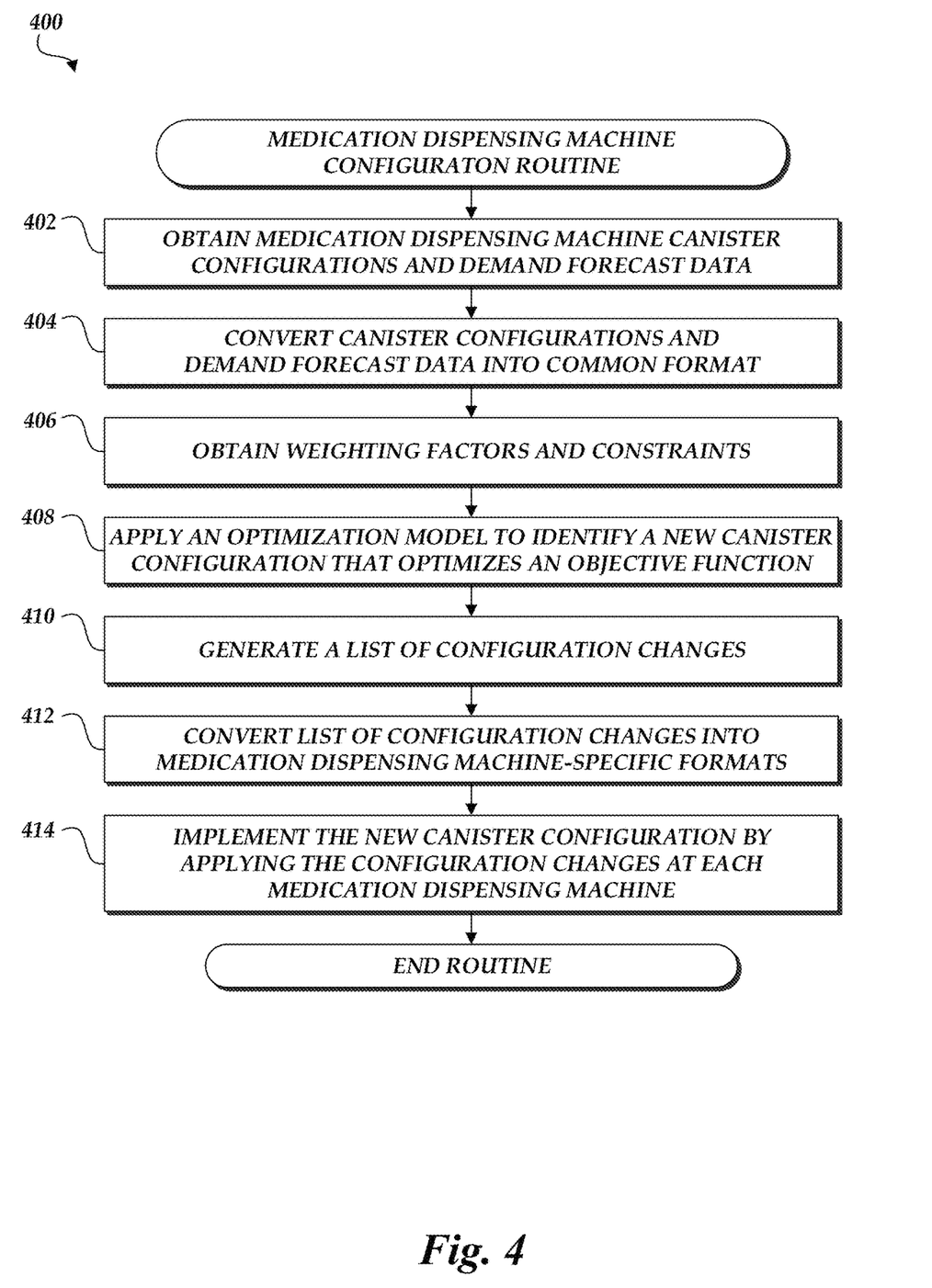
FIG. 4 is a flowchart depicting an example routine for configuring a medication dispensing machine in accordance with aspects of the present disclosure.

FIG. 4 is a flow diagram depicting an example medication dispensing machine configuration routine 400 that may be implemented in accordance with aspects of the present disclosure. The routine 400 may be carried out, for example, by the canister configuration system 104 depicted in FIG. 1. The routine 400 beings at block 402, where existing canister configurations and demand forecast data may be obtained for one or more medication dispensing machines. In some embodiments, medication dispensing machines may be organized or categorized into groups, and the routine 400 may be carried out on a per-group basis or may determine configurations for different groups based on the total dispensed medications across all the groups. In some embodiments, demand forecast data may be obtained on a per-dispensing machine basis (e.g., by obtaining dispensed medication data from each medication dispensing machine). In other embodiments, an overall demand forecast may be obtained or generated.

At block 404, in some embodiments, canister configurations and demand forecast data may be converted into a common format. Illustratively, medication dispensing machines may be sourced from different manufacturers, and may report their configurations and data regarding dispensed medications in different formats. The routine 400 may thus convert these formats to a common format to enable comparisons and analyses. In some embodiments, the common format may correspond to the format generated by dispensing machines from a particular manufacturer, and thus block 404 may be omitted for configurations and data obtained from dispensing machines from that manufacturer.

At block 406, weighting factors, constraints, and other inputs to an optimization model may be obtained. As described in more detail above with reference to FIG. 3, the weighting factors may correspond to measured or estimated performance impacts of actions such as canister swaps, tray fills, configuring canisters, and the like. Similarly, as discussed above, the constraints on the output of the optimization model may include limits on the number of changes or the amount of time to be spent implementing the changes, restrictions on how particular medications are dispensed, and the like.

At block 408, the optimization model may be applied to generate an updated canister configuration that seeks to optimize a function that incorporates the weighting factors obtained at block 406. As described above, the optimization model may, in some embodiments, seek to solve a mixed-integer linear programming problem to optimize an objective function that incorporates the weighting factors. In some embodiments, a single canister configuration may be generated for all medication dispensing machines from which data was obtained at block 402. In other embodiments, different canister configurations may be generated for each dispensing machine, for each group of dispensing machines, each type of dispensing machine, and combinations thereof.

At block 410, a list of configuration changes may be generated. Illustratively the list of configuration changes may include detailed instructions on how to reconfigure a medication dispensing machine from the existing canister configuration obtained at block 402 to the updated canister configuration generated at block 408. In further embodiments, the list of configuration changes may identify medications to be loaded into canisters, medications to be unloaded from canisters, canisters to be loaded into "fixed" (reserved) slots on the dispensing machine, canisters to be initially loaded into "flex" slots that are designated for swapping in canisters, and the like. It will be understood that designations such as "fixed" and "flex" represent operational definitions of how the slot is utilized during operation of the dispensing machine, and that the slot itself is not necessarily reconfigured or changed in function.

At block 412, in some embodiments, the list of configuration changes generated at block 410 may be converted into formats that are specific to particular medication dispensing machines. Illustratively, the procedures for configuring a dispensing machine may vary by manufacturer, location, or other criteria. The routine 400 may therefore convert all or part of the list from a common format to a machine-specific format. In some embodiments, converting to a dispensing machine-specific format may complement or reverse the conversion into a common format that was carried out at block 404.

At block 414, the updated canister configuration may be implemented by applying the configuration changes from the list generated at block 410. In some embodiments, the updated configuration may be implemented by transmitting the list of configuration changes to an operations team, which may reconfigure the dispensing machines. In other embodiments, all or part the updated canister configuration may be implemented automatically.

It will be understood that FIG. 4 is provided for purposes of example, and that many variations on the depicted routine 400 are within the scope of the present disclosure. For example, block 406 may be carried out at any time prior to block 408, and in some embodiments may be carried out prior to the routine 400. As a further example, block 410 may be omitted and the updated canister configuration may be provided without generating a list of changes from the previous configuration. FIG. 4 is thus understood to be illustrative and not limiting.

Figure 5:
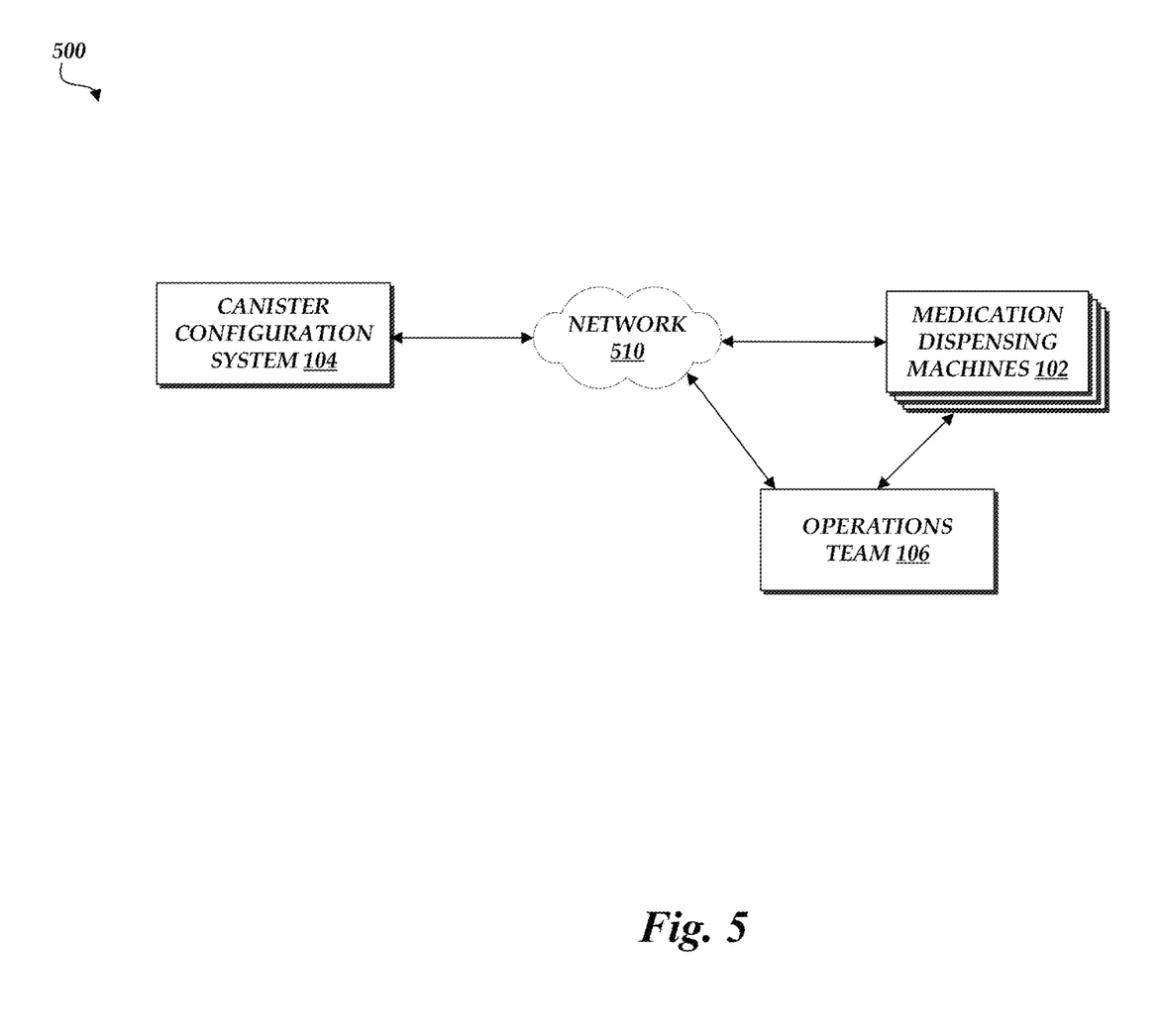
FIG. 5 is a block diagram depicting an example network environment in which a canister configuration system may communicate with medication dispensing machines and operations computing devices in accordance with aspects of the present disclosure.

FIG. 5 is a block diagram of an example network environment 500 in which a canister configuration system 104 may operate and communicate with medication dispensing machines 102 and an operations team 106. It will be understood that the network environment 500 may include more (or fewer) elements than those shown in FIG. 5. It is not necessary, however, that all of these elements be shown in order to provide an enabling disclosure.

The network environment 500 may include a canister configuration system 104, which is described in more detail with reference to FIG. 6 below. The canister configuration system 104 may communicate with medication dispensing machines 102 and operations team(s) 106 via a network 510, which may illustratively be any wired or wireless network, or combination thereof. In addition, the network 510 may include, but is not limited to, a cellular telecommunications network, Wi-Fi network, cable network, satellite network, mesh network, personal area network, local area network (LAN), wide area network (WAN), public or private intranet, the Internet, or other public or private communications network or networks, or any combination thereof. In some embodiments, the network 510 may be a private or semi-private network, such as a corporate or university intranet. The network 510 may include one or more wireless networks, such as a Global System for Mobile Communications (GSM) network, a Code Division Multiple Access (CDMA) network, a Long Term Evolution (LTE) network, or some other type of wireless network. The network 510 may use protocols and components for communicating via the Internet or any of the other aforementioned types of networks. In some embodiments, the network 510 may be omitted, and one or more of the canister configuration systems 104, medication dispensing machines 102, or operations teams 106 may communicate directly with each other.

The medication dispensing machines 102 are described in more detail above with reference to FIG. 2, and may generally include any machine that dispenses medications in accordance with aspects of the present disclosure. While the present disclosure makes reference to dispensing machines 102 having slots, canisters, and trays, it will be understood that the present disclosure is not limited to dispensing machines 102 having these properties, and that embodiments of the present disclosure include dispensing machines 102 having other mechanisms for dispensing medications.

The example network environment 500 further includes an operations team 106, which receives canister configurations and implements them by interacting with the medication dispensing machines 102. The operations team 106 may include a computing device that interacts with the canister configuration system 104 via the network 510. Examples of computing devices that may serve as an operations team 106 computing device include personal computing devices, laptop computing devices, mobile computing devices, tablet computing devices, wearable computing devices, interactive media devices, smart appliances, thin clients, gaming devices, and the like. In some embodiments, the operations team 106 may interact directly with the canister configuration system 104 (e.g., without going through a network 510).

Figure 6:
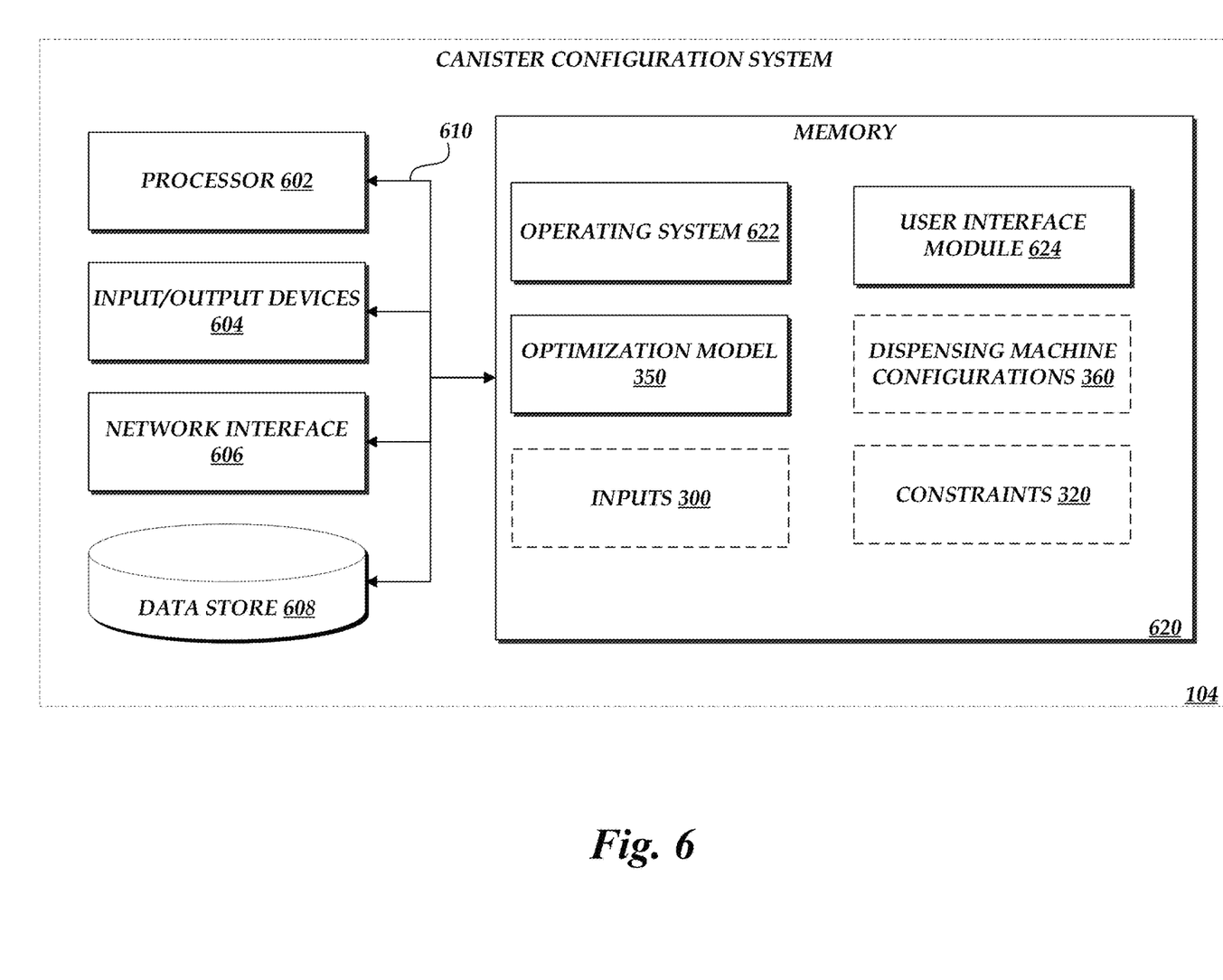
FIG. 6 depicts a general architecture of a computing device that may implement a canister configuration system in accordance with aspects of the present disclosure.

FIG. 6 depicts a general architecture of the canister configuration system 104, which includes an arrangement of computer hardware and software configured to implement aspects of the present disclosure. The canister configuration system 104 may include many more (or fewer) elements than those shown in FIG. 6. It is not necessary, however, that all of these generally conventional elements be shown in order to provide an enabling disclosure.

In the depicted embodiment, the canister configuration system 104 includes a processor 602, input/output device interfaces 604, a network interface 606, and a data store 608, all of which may communicate with one another by way of a communication bus 610. The network interface 606 may provide connectivity to one or more networks or computing systems. The processor 602 may thus receive information and instructions from other computing systems or services via a network. The processor 602 may also communicate to and from a memory 620 and further provide output information for an optional display (not shown) via the input/output device interfaces 604. The input/output device interfaces 604 may also accept input from an optional input device (not shown). The data store 608 may generally be any non-transitory computer-readable data store, including but not limited to hard drives, solid state devices, magnetic media, flash memory, and the like. In some embodiments, the data store 608 may be implemented as a database, web service, or cloud computing service, and may be external to the canister configuration system 104. Additionally, in various embodiments, the data store 608 may be implemented as a single data store or distributed across multiple data stores.

The memory 620 may contain computer program instructions (grouped as modules in some embodiments) that the processor 602 executes in order to implement one or more aspects of the present disclosure. The memory 620 generally includes random access memory (RAM), read only memory (ROM) and/or other persistent, auxiliary or non-transitory computer readable media. The memory 620 may store an operating system 622 that provides computer program instructions for use by the processor 602 in the general administration and operation of the canister configuration system 104. The memory 620 may further include computer program instructions and other information for implementing aspects of the present disclosure. For example, in one embodiment, the memory 620 includes a user interface module 624 that generates interfaces (and/or instructions therefor) for configuring the canister configuration system 104. In addition, the memory 620 may include and/or communicate with one or more data repositories (not shown), for example, to access user program codes and/or libraries.

In the illustrated embodiment, the memory 620 further includes an optimization model 350. The optimization model 350, as described in more detail above with reference to FIG. 3, may generate dispensing machine configurations 360 based on inputs 300 and constraints 320, which may be loaded into the memory 620 as needed. In various embodiments, the inputs 300 and constraints 320 may be obtained via the user interface module 624, loaded from the data store 608, received via the network interface 606, or combinations thereof.

In some embodiments, the canister configuration system 104 may include further components in addition to those illustrated in FIG. 6. For example, the memory 620 may include a module that generates a list of changes by comparing an updated canister configuration to a previous canister configuration. As a further example, the memory 620 may include a format conversion module that converts data received from dispensing machines into a common format and vice versa. FIG. 6 is thus understood to be illustrative but not limiting.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules, including one or more specific computer-executable instructions, that are executed by a computing system. The computing system may include one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might," or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

What is claimed is:

1. A system comprising:
a data store configured to store computer-executable instructions; and
a processor in communication with the data store, wherein the computer-executable instructions, when executed by the processor, configure the processor to perform operations including:
obtaining configuration information for each of a plurality of medication dispensing machines, wherein the configuration information identifies a plurality of medications that the medication dispensing machine is configured to dispense, and wherein each of the plurality of medications is stored in a respective canister that is loaded into a slot of the medication dispensing machine;
converting the configuration information into a common format to produce converted configuration information;
generating a demand forecast of medications predicted to be dispensed, the demand forecast based at least on quantities of medications dispensed by each of the plurality of medication dispensing machines during a specified time period;
determining, based at least in part on the converted configuration information, the demand forecast, and a set of weighting factors, an updated configuration for the plurality of medication dispensing machines, the updated configuration including, for each medication dispensing machine:
a fixed set of medications, wherein the medication dispensing machine is to be loaded with a canister of each of the fixed set of medications,
a swappable set of medications, wherein the medication dispensing machine is to load a canister of a medication in the swappable set in response to demand for the medication, and
a tray-fill set of medications, wherein the medication dispensing machine is to dispense a medication in the tray-fill set from a tray rather than a canister;
converting the updated configuration information for each of the plurality of medication dispensing machines into one or more specific formats for the one or more medication dispensing machines to produce a converted updated configuration; and
transmitting the converted updated configuration, wherein transmitting the updated configuration causes each of the plurality of medication dispensing machines to be configured in accordance with the updated configuration.

2. The system of claim 1, wherein the data store is configured to store further computer-executable instructions that, when executed by the processor, configure the processor to perform further operations including obtaining capacity information for each of the plurality of medication dispensing machines, the capacity information including a maximum quantity of canisters that each medication dispensing machine can hold.

3. The system of claim 1, wherein a first weighting factor in the set of weighting factors is associated with one or more of swapping a canister, dispensing a medication from a tray, manually dispensing a medication, converting a medication from tray fill to canister fill, or converting a medication from canister fill to tray fill.

4. The system of claim 1, wherein the data store is configured to store further computer-executable instructions that, when executed by the processor, configure the processor to generate the set of weighting factors based at least in part on performance metrics associated with the quantities of medications dispensed by each of the plurality of medication dispensing machines during the specified time period.

5. The system of claim 1, wherein the updated configuration identifies a subset of the swappable set of medications to be initially loaded into each of the plurality of medication dispensing machines.

6. A computer-implemented method under control of a computing device configured with specific computer-executable instructions, the computer-implemented method comprising:

obtaining configuration information for one or more medication dispensing machines, wherein the configuration information identifies, for a medication dispensing machine of the one or more medication dispensing machines, a plurality of medications that the medication dispensing machine is configured to dispense, wherein each of the plurality of medications is stored in a respective canister, and wherein the medication dispensing machine comprises a predefined quantity of canister slots;

converting the configuration information into a common format to produce converted configuration information;

generating a demand forecast based at least in part on quantities of medications dispensed by each of the one or more medication dispensing machines during a specified time period;

determining an updated configuration for each of the one or more medication dispensing machines based at least in part on the converted configuration information, the demand forecast, and a set of weighting factors, wherein each updated configuration defines a plurality of dispensing groups, and wherein each of the plurality of dispensing groups is associated with a method of dispensing and a respective set of medications;

converting the updated configuration information for each of the one or more medication dispensing machines into one or more specific formats for the one or more medication dispensing machines to produce a converted updated configuration; and outputting the converted updated configuration, wherein outputting the updated configuration causes each of the one or more medication dispensing machines to be configured in accordance with the updated configuration.

7. The computer-implemented method of claim 6, wherein the plurality of dispensing groups includes one or more of a fixed dispensing group, a swappable dispensing group, a tray-fill dispensing group, or a manual dispensing group.

8. The computer-implemented method of claim 6, wherein the updated configuration is determined based at least in part on the plurality of medications that each of the one or more medication dispensing machines is currently configured to dispense.

9. The computer-implemented method of claim 6, wherein determining the updated configuration comprises applying a mixed-integer linear programming algorithm.

10. The computer-implemented method of claim 6, wherein the updated configuration for the one or more medication dispensing machines includes a first configuration for the medication dispensing machine and a second configuration for a second medication dispensing machine.

11. The computer-implemented method of claim 10, wherein the first configuration includes a first fixed dispensing group and the second configuration includes a second fixed dispensing group.

12. The computer-implemented method of claim 10, wherein the updated configuration is determined based at least in part on a set of constraints.

13. The computer-implemented method of claim 12, wherein the set of constraints includes one or more of: a maximum number of canisters to be configured, a maximum number of canister swaps to be performed when configuring the one or more medication dispensing machines, a maximum time duration to be spent configuring the one or more medication dispensing machines, a minimum or maximum quantity of fixed canisters per medication dispensing machine, a minimum or maximum quantity of swappable canisters per medication dispensing machine, or a maximum number of medication dispensing machines per shipment.

14. The computer-implemented method of claim 12, wherein the set of constraints includes a set of controlled substance medications, and wherein medications in the set of controlled substance medications may not be included in a fixed and/or swappable dispensing group.

15. The computer-implemented method of claim 6, wherein the demand forecast comprises a plurality of medication orders, and wherein individual orders of the plurality of medication orders identify one or more medications dispensed in that order.

16. The computer-implemented method of claim 15, wherein the updated configuration is determined based at least in part on a set of constraints, and wherein the set of constraints includes that, for each medication order in the demand forecast, at least one medication dispensing machine be configured to fulfill the order.

17. A non-transitory computer-readable medium comprising computer-executable instructions that, when executed by a processor, configure the processor to perform operations including:

obtaining configuration information for a medication dispensing machine, the configuration information identifying a plurality of medications that the medication dispensing machine is configured to dispense, and wherein each of the plurality of medications is stored in a respective container that is loaded into the medication dispensing machine;

converting the configuration information into a common format to produce converted configuration information;

determining an updated configuration for the medication dispensing machine based at least in part on the configuration information, a set of weighting factors, and a demand forecast, wherein the updated configuration defines a plurality of dispensing groups, and wherein each of the plurality of dispensing groups is associated with a method of dispensing and a respective set of medications;

converting the updated configuration information for the medication dispensing machine into one or more specific formats for the one or more medication dispensing machines to produce a converted updated configuration; and causing the medication dispensing machine to be configured in accordance with the converted updated configuration.

18. The non-transitory computer-readable medium of claim 17, wherein the non-transitory computer-readable medium comprises further computer-executable instructions that, when executed by the processor, configure the processor to perform further operations including generating the demand forecast based at least in part on dispensed medication data.

19. The non-transitory computer-readable medium of claim 17, wherein the updated configuration defines the plurality of dispensing groups by identifying a set of changes to the configuration of the medication dispensing machine.

20. The non-transitory computer-readable medium of claim 17, wherein the plurality of dispensing groups includes a tray-filled dispensing group.

\* \* \* \* \*

UNITED STATES PATENT AND TRADEMARK OFFICE
CERTIFICATE OF CORRECTION

| | |
|---|---|
| PATENT NO. | : 11,996,185 B1 |
| APPLICATION NO. | : 17/449415 |
| DATED | : May 28, 2024 |
| INVENTOR(S) | : Elcin Cetinkaya |

It is certified that error appears in the above-identified patent and that said Letters Patent is hereby corrected as shown below:

On the Title Page

Item (72), Inventors, after "Richard Voskoboynikov, Pembroke Pines, FL (US)"; add – Tyler Wortman, Scottsdale, AZ (US) –.

In the Specification

In Column 6, Line 60, delete "capacity" and insert -- capacity. --.

Signed and Sealed this
Eighth Day of October, 2024

Katherine Kelly Vidal
*Director of the United States Patent and Trademark Office*